US009562888B2

(12) United States Patent
Parpia et al.

(10) Patent No.: US 9,562,888 B2
(45) Date of Patent: Feb. 7, 2017

(54) STRESS-BASED SENSOR, METHOD, AND APPLICATIONS

(75) Inventors: Jeevak M. Parpia, Ithaca, NY (US); Harold G. Craighead, Ithaca, NY (US); Darren R. Southworth, Munich (DE); Leon M. Bellan, Somerville, MA (US)

(73) Assignee: CORNELL UNIVERSITY, Ithaca, NY (US)

( * ) Notice: Subject to any disclaimer, the term of this patent is extended or adjusted under 35 U.S.C. 154(b) by 429 days.

(21) Appl. No.: 13/637,861

(22) PCT Filed: Mar. 31, 2011

(86) PCT No.: PCT/US2011/030673
§ 371 (c)(1),
(2), (4) Date: Jan. 15, 2013

(87) PCT Pub. No.: WO2011/162847
PCT Pub. Date: Dec. 29, 2011

(65) Prior Publication Data
US 2013/0118228 A1    May 16, 2013

Related U.S. Application Data

(60) Provisional application No. 61/319,369, filed on Mar. 31, 2010.

(51) Int. Cl.
*G01N 33/497* (2006.01)
*G01N 29/02* (2006.01)

(52) U.S. Cl.
CPC .......... *G01N 33/497* (2013.01); *G01N 29/022* (2013.01)

(58) Field of Classification Search
CPC .................................................. G01N 33/497
(Continued)

(56) References Cited

U.S. PATENT DOCUMENTS 4,463,610 A * 8/1984 Anderson et al. ............... 73/654
4,479,389 A * 10/1984 Anderson et al. ............... 73/651
(Continued)

FOREIGN PATENT DOCUMENTS

WO    2005029042 A2    3/2005

OTHER PUBLICATIONS

Zalalutdinov et al., "Single Crystal Diamond Nanomechanical Dome Resonator", 2008 NRL Review, pp. 190-191, 2008.*
(Continued)

*Primary Examiner* — Peter Macchiarolo
*Assistant Examiner* — Alexander Mercado
(74) *Attorney, Agent, or Firm* — Bond, Schoeneck & King, PLLC; William Greener

(57) ABSTRACT

A composite, analyte sensor includes a substrate; a micro- or nano-electro-mechanical (MEMS; NEMS) resonator that is coupled to the substrate at least two edge locations (i.e., it is at least doubly-clamped) of the resonator, wherein the resonator is in a statically-buckled state near a buckling transition point of the resonator; and a chemically-responsive substance covering at least a portion of the surface of the resonator that will undergo a conformational change upon exposure to a given analyte. The resonator may be a double-clamped, statically-buckled beam (or bridge), a multiply-clamped, statically-buckled dome (or crater), or other resonator geometry. The sensor may include two or more at least double-clamped, statically-buckled, composite MEMS or NEMS resonators each operating near a buckling transition point of the respective resonator, and each characterized by a different resonant frequency. A method for sensing an analyte in ambient air.

10 Claims, 11 Drawing Sheets

(58) Field of Classification Search
USPC .................................. 73/23.3, 23.2–31.07
See application file for complete search history.

(56) References Cited

U.S. PATENT DOCUMENTS

| | | | |
|---|---|---|---|
| 5,090,254 A * | 2/1992 | Guckel et al. ............. | 73/862.59 |
| 5,188,983 A * | 2/1993 | Guckel et al. ................. | 438/53 |
| 6,289,717 B1 | 9/2001 | Thundat et al. | |
| 7,300,631 B2 | 11/2007 | Miller et al. | |
| 7,398,671 B2 | 7/2008 | Brederlow et al. | |
| 7,409,851 B2 | 8/2008 | Ilic et al. | |
| 7,498,720 B2 | 3/2009 | Loebl et al. | |
| 7,598,094 B2 | 10/2009 | Masters et al. | |
| 7,611,908 B2 | 11/2009 | Miller et al. | |
| 7,629,137 B2 | 12/2009 | Sauer-Budge et al. | |
| 7,648,844 B2 | 1/2010 | Srivastava et al. | |
| 7,673,517 B2 | 3/2010 | Stievater et al. | |
| 7,679,563 B2 | 3/2010 | Werner et al. | |
| 2002/0137084 A1 | 9/2002 | Quate et al. | |
| 2002/0190603 A1* | 12/2002 | Ma et al. ...................... | 310/309 |
| 2003/0215865 A1 | 11/2003 | Mayer et al. | |
| 2004/0093947 A1 | 5/2004 | Brederlow et al. | |
| 2005/0112621 A1 | 5/2005 | Kim et al. | |
| 2005/0164289 A1 | 7/2005 | Quate et al. | |
| 2010/0000292 A1* | 1/2010 | Karabacak et al. ......... | 73/24.01 |
| 2010/0107285 A1 | 4/2010 | Ekinci et al. | |
| 2010/0139406 A1 | 6/2010 | Stievater et al. | |
| 2010/0190270 A1 | 7/2010 | Piazza et al. | |
| 2013/0118228 A1* | 5/2013 | Parpia et al. .................. | 73/23.3 |

OTHER PUBLICATIONS

Goeders, Karen M., Jonathan S. Colton, and Lawrence A. Bottomley. "Microcantilevers: sensing chemical interactions via mechanical motion." Chemical reviews 108.2 (2008): 522-542.*

Nicu, L., and C. Bergaud. "Experimental and theoretical investigations on nonlinear resonances of composite buckled microbridges." Journal of applied physics 86.10 (1999): 5835-5840.*

Korotcenkov, Ghenadii. Handbook of Gas Sensor Materials Properties, Advantages and Shortcomings for Applications vol. 2: New Trends and Technologies., p. 187, accessed May 3, 2016.*

Gupta et al.; Anomalous Resonance in a Nanomechanical Biosensor; http://www.pnas.org/content/103/36/13362.full; 2005; 1-4.

Dufour et al.; Signal-to-noise ratio of resonant microcantilever type chemical sensors as a function of resonant frequency and quality factor; Sensors and Actuators B. vol. 102, No. 1, pp. 73-77. Sep. 1, 2004.

Ilic et al.; Enumeration of DNA Molecules Bound to a Nanomechanical Oscillator; Nano Lett., 2005, 5 (5), pp. 925-929.

Southworth et al.; Stress-based vapor sensing using resonant microbridges | Browse—Applied Physics Letters; Appl. Phys. Lett. 96, 163503 (2010); doi:10.1063/1.3393999 (3 pages).

* cited by examiner

STRESS-BASED SENSOR, METHOD, AND APPLICATIONS

RELATED APPLICATION DATA

The instant application claims priority to U.S. Provisional application Ser. No. 61/319,369 filed on Mar. 31, 2010, the subject matter of which is incorporated herein by reference in its entirety.

GOVERNMENT FUNDING

This invention was made with Government support under DMR-0908634 awarded by the National Science Foundation and HR-00011-06-1-0042 awarded by DARPA. The United States Government has certain rights in the invention.

BACKGROUND

1. Field of the Invention

Embodiments of the invention are in the field of analyte sensors, more particularly, micro- or nano-electro-mechanical (MEMS; NEMS) resonator-based sensors and, most particularly, MEMS/NEMS, statically-buckled resonator-based sensors, methods of making, and applications thereof.

2. Related Art

A need exists for fast and inexpensive trace vapor detectors. Microsensors based on electrochemical, surface acoustic wave, optical, and mechanical transduction are under investigation to meet this demand. Sensors based on micro-electromechanical systems (MEMS) are candidates for a wide range of sensing applications including environmental monitoring; biological, biomedical and biochemical analysis; health monitoring; and detection of explosives for security use and landmine sweeping.

Microcantilevers have been the primary MEMS structures used in sensors research. FIGS. 1A, 1B schematically illustrate, respectively, a MEMS cantilever with a reactive coating on multiple sides corresponding to a resonant mode and, on a single side corresponding to a deflection mode. Changes in the resonance frequency of the cantilever due to the added mass of analyte or changes in materials properties due to chemical interaction between the analyte and a reactive coating are measured using these devices. Gravimetric mass sensors have proven extremely sensitive in vacuum. Various surface coatings and treatments have been developed for use at ambient pressure where sensitivity is lower due to viscous losses. Alternately, cantilevers are coated on a single side with a reactive layer that swells or contracts upon contact with an analyte and a static deflection is measured. In functionalized cantilever studies, deflection of the composite structure relieves the stress induced by these volumetric changes.

Breath gas analysis is a well documented technology that uses a variety of techniques spanning the scale from proton-transfer-reaction mass spectrometry and ion-molecule-reaction mass spectrometry, to the deflection of cantilevers. The prospect of directly analyzing 'breath gas' for various volatile organic compounds (VOCs) raises the possibility of monitoring human performance and stress, as well as enabling a broad-based non-invasive tool for diagnosis and monitoring.

Breath gas components acetaldehyde, acetone, ethanol, isoprene have been monitored, with isoprene in particular correlated to heart rate. Acetaldehyde, an oxidation product of ethanol, is seen to decrease during sleep, while isoprene is related to the biosynthesis of cholesterol and shows a time variation during sleep correlated to heart rate. Other gasses, e.g., o-toluidine, show correlation to lung carcinoma. Thus it is well established that by measuring various volatile organic compounds, important physiological information can be obtained from the breath of human subjects. The typical range of relevant gas concentrations are 100s to 1000s of ppb.

Prior technology pioneered the use of the time dependent deflection of a cantilever array on which a variety of polymer coatings were deposited to resolve the presence of VOCs using principal component analysis (a 'NOSE'). The analysis also demonstrated success in resolving signatures from various alcohols (from heptanol to methanol), as well as acetone, toluene, dichloromethane and heptane. Response times were relatively rapid (on the order of a few seconds). The 'NOSE' was used to carry out a neural network analysis of various natural flavors (M. K. Baller, H. P. Lang, J. Fritz, Ch. Gerber, J. K. Gimzewski, U. Drechsler, H. Rothuizen, M. Despont, F. M. Battiston, J. P. Ramseyer, P. Formaro, E. Meyer, J. J. Guntehrrodt, "A cantilever array-based artificial nose", Ultramicroscopy 82 1-9 (2000)).

FIGS. 2(*a-d*) show data published by the same group on the response of a cantilever array to breath gas from two healthy patients (a, b) and two patients with renal disease (uraemia) (c, d). A compound found in patient's breath associated with uraemia is dimethylamine, which is presumably the sensed VOC. It is noted that the detection response time in the 100s of seconds (H. P. Lang, J. P. Ramseyer, W. Grange, T. Braun, D. Schmid, P. Hunziker, C. Jung, M. Hegner, C. Gerber "An Artificial Nose Based on Microcantilever Array Sensors", Journal of Physics: Conference Series 61 (2007) 663-667 doi:10.1088/1742-6596/61/1/133 International Conference on Nanoscience and Technology (ICN&T 2006)).

Other studies have compared resonant frequency shifts and cantilever deflection as a methodology for signal extraction. The VOC sensed was RDX vapor on a carboxyl-terminated self-assembled mono-layer (SAM) of 4-mercaptobenzoic acid (4-MBA aka thiosalicylic acid) (Thomas Thundat, Lal Pinnaduwage and Richard Lareau, "Explosive Vapour Detection using micromechanical sensors" in Electronic Noses & Sensors for the Detection of explosives, 249-266, J. W. Gardner and J. Yimon, eds. Kluwer (Netherlands) (2004)). FIG. 3 (their result) shows negligible sensitivity of the resonant frequency to RDX vapor in contrast to the robust signal from deflection. The deflection of the cantilever is attributed to stress in the SAM that induces bending in the cantilever. The same group also demonstrated mass absorption induced frequency shift at the 15 pg level of PETN on their 4-MBA functionalized cantilever; resolution was estimated at the few pg level.

Resonant cantilevers were used without functionalization to demonstrate sensitivity to ethanol (S-J. Kim, T Ono, M. Esashi, "Mass detection using capacitive resonant silicon resonator employing LC resonant technique" Rev. Sci. Instr., 78 085103-1-6 (2007)). In that study, the researchers hypothesized that the increase in resonant frequency observed (100 Hz shift compared to 81 kHz frequency) with a Q=10 in ambient air when the cantilever was exposed to moisture in the air was due to a change in stress in the native oxide layer on the cantilever's surface. In contrast, exposure to ethanol laden air evoked a negative frequency shift due to adsorption of the ethanol vapor. The concentrations of analytes were 1400 ppm (water) and unknown for the ethanol.

Cantilever deflection by exposure to DNT via diffusion of the VOC into a nano-porous material, TBC6A (thickness 300 to 500 nm) has also been demonstrated (P. G. Datskos, N. V. Lavrik, and M. J. Sepaniak, "Detection of Explosive Compounds with the Use of Microcantilevers with Nanoporous Coatings", Sensor Letters, 1, 25-32, (2003)). In that study, a µm thick coating of TBC6A was deposited by thermal evaporation on a cantilever. The cantilevers were able to resolve the presence of TNT and its various derivatives. However, the response time was excessively long, though the researchers were able to demonstrate improvement in the response time by elevating the temperature of the substrate.

The same group demonstrated a true "nose" similar to the Baller et al. work referred to above by thermally evaporating various organic compounds on nanostructured gold surfaces. They demonstrated a deflection response to a variety of VOCs from $CO_2$ to tri- and tetra-chlorethylene via nine different coatings thermally evaporated onto a cantilever array. The responses were examined with an artificial neural network (ANN) algorithm, enabling identification of individual components as well as the ability to assay them from a mixture (P. G. Datskos, N. V. Lavrik, M. J. Sepaniak, and P. Dutta, "Chemical sensors based on functionalized microcantilever arrays", IEEE sensors Exco Korea Oct 22 862-867, (2006) and C. A. Tipple, N. V. Lavrik, M. Cuha, J. Headrick, P. Datskos, and M. J. Sepaniak, "Nanostructured Microcantilevers with functionalized cyclodextrin receptor phases: Self assembled monolayers and vapor deposited films", Anal. Chem., 74, 3118-3126 (2004)).

The methodology of ANN or Principal Component Analysis (PCA) is similar to that employed in commercial handheld noses that rely on mass adsorption and resonant frequency shift of quartz crystal microbalances (Quartz Crystal Monitors-QCMs). Though the various coatings of the QCMs are proprietary, it is hypothesized that as long as there is a differential response to various analytes, coatings can be relatively simple. It is clear that the distinguishing feature of the QCM vs. cantilever responses in terms of the resonant frequency shift is the fact that cantilevers are highly dissipative in air, thus relinquishing their surface area/volume advantage over QCMs, which have relatively high Qs in ambient air at the expense of poor surface/volume. Most commercial handheld noses use four to eight sensors, cost between 10000 and 25000 USD, and require battery power that is limited to a few hours of operation.

In view of the foregoing discussion as well as other information known in the art, the inventors have recognized the benefits and advantages that would be provided over cantilever-based sensors, QCMs used in current VOC monitors, and lab-based gas chromatography by sensor apparatus and methods that operate more rapidly (seconds vs. minutes) due to reduced thickness of the functionalizing film, especially for nano-porous materials, and comparable to the time constant of delivery of the gas to the sensor; that ease the readout of the sensor (e.g., frequency rather than deflection, with no requirement for the large dimensions needed for the optical measurement of deflection). That can provide a miniaturized array of sensors on a chip scale; that have reduced cost, size, and power requirements; and others. Besides medical applications, such devices could also find utility in a variety of consumer applications from food packaging to cosmetics, and defense applications ranging from explosives detection to munitions monitoring.

SUMMARY

An embodiment of the invention is directed to a composite, analyte sensor. In an exemplary aspect, the sensor includes a substrate; a micro- or nano-electro-mechanical (MEMS; NEMS) resonator that is coupled to the substrate at least two edge locations (i.e., it is at least doubly-clamped) of the resonator, wherein the resonator is in a statically-buckled state near a buckling transition point of the resonator; and a chemically-responsive substance covering at least a portion of the surface of the resonator that will undergo a conformational change upon exposure to a given analyte. In a non-limiting aspect, the resonator is a double-clamped, statically-buckled beam (or bridge). In another aspect, the resonator is a multiply-clamped, statically-buckled dome (or crater). Other resonator geometries satisfying the conditions recited herein above may be used. In a non-limiting aspect, the sensor includes two or more at least double-clamped, statically-buckled, composite MEMS or NEMS resonators each operating near a buckling transition point of the respective resonator, and each characterized by a different resonant frequency. A sensor assembly may include other components such as, but not limited to, a housing(s), a resonator drive source(s), a readout(s), a user interface(s), and others whose uses are known and would be obvious to those skilled in the art; however, these are not considered the invention per se.

Another, related embodiment of the invention is directed to a method for sensing an analyte in ambient air. In an exemplary aspect, the method includes the steps of providing an at least double-clamped, statically-buckled, composite micro- or nano-electro-mechanical (MEMS; NEMS) resonator that is buckled near a buckling transition point of the resonator; driving the resonator to resonate at a resonance frequency; exposing the structure to a given air sample; and, measuring a change in the resonance frequency of the resonator at a selected time after exposing the resonator to the given air sample. The change in resonant frequency may then be used to determine an amount of the analyte in the air sample. The analyte may be sensed in a time period less than a few seconds and, particularly, in less than one second, limited in our experiments by the time required to exchange the air in the flow cell. In an aspect, a plurality of at least double-clamped, buckled, composite MEMS or NEMS resonators each operating near a buckling transition point of the respective resonator, and each of which are resonating at a different resonant frequency may be provided. The method may include exposing the resonating resonator to a breath sample of a living subject.

As used herein, the term 'composite' means that the active device component (i.e., the clamped, buckled resonator) is as least partially coated with a selected reactive coating appropriately chosen for the analyte to be sensed.

In general, volumetric changes in the reactive coating layer (e.g., swelling, expansion, contraction) on the resonator due to the presence of the analyte will alter the compression in the device, leading to large and rapid changes in the resonance frequency. The stress, S, can be quantifiably measured by tracking shifts in the resonance frequency.

In various non-limiting aspects, the resonator may be of any of a wide variety of materials including but not limited to polycrystalline silicon, silicon nitride, ceramic, plastic, and metal. In a particular aspect, the device layer (resonator) thickness will advantageously be less than one micrometer (1µ). The use of a material that is electrically conductive or made conductive by inclusion of an additional metal layer will facilitate electrical detection of the device motion.

In an aspect, reactive coating layer thickness will be less than about 10× the device layer thickness, such that the coating layer not dominate the resonant motion of the device. If the sensing layer is soft compared to the device layer (i.e., plastic vs. silicon), the effect on the over-all Young's Modulus (i.e., stiffness, and thus resonant frequency) will be small enough to be ignored.

In an exemplary aspect, a statically-buckled microbridge (25×6×0.12 μm) was fabricated from a compressively-stressed polysilicon film grown by low pressure chemical vapor deposition (LPCVD) over a sacrificial oxide layer. Upon wet-etch release of a doubly-clamped bridge, the residual stress was relieved by buckling of the structure.

Additional features and advantages of the invention will be set forth in the detailed description which follows, and in part will be readily apparent to those skilled in the art from that description or recognized by practicing the invention as described herein, including the detailed description which follows, the claims, as well as the appended drawings.

It is to be understood that both the foregoing general description and the following detailed description are merely exemplary of the invention, and are intended to provide an overview or framework for understanding the nature and character of the invention as it is claimed. The accompanying drawings are included to provide a further understanding of the invention, and are incorporated in and constitute a part of this specification. The drawings illustrate various embodiments of the invention, and together with the description serve to explain the principles and operation of the invention.

DETAILED DESCRIPTION OF EXEMPLARY EMBODIMENTS OF THE INVENTION

In the following description, reference is made to the accompanying drawings that form a part hereof, and in which are shown by way of illustration specific embodiments that may be practiced. These embodiments are described in sufficient detail to enable those skilled in the art to practice the invention, and it is to be understood that other embodiments may be utilized and that structural, logical, and electrical changes may be made without departing from the scope of the present invention. The following description of example embodiments is, therefore, not to be taken in a limited sense.

Figure 1:
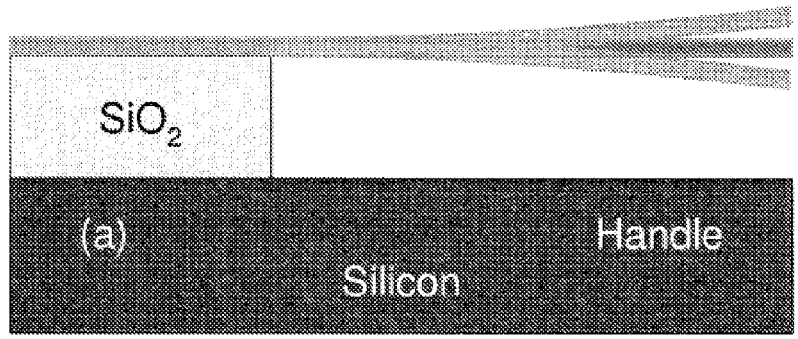
FIGS. 1A, 1B schematically illustrate, respectively, a MEMS cantilever with a reactive coating on multiple sides corresponding to a resonant mode and, on a single side corresponding to a deflection mode, according to the prior art.
Figure 1:
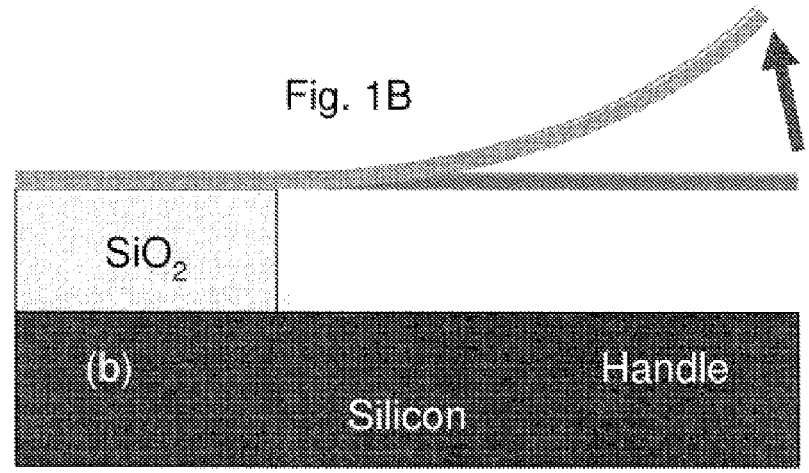
Figure 2:
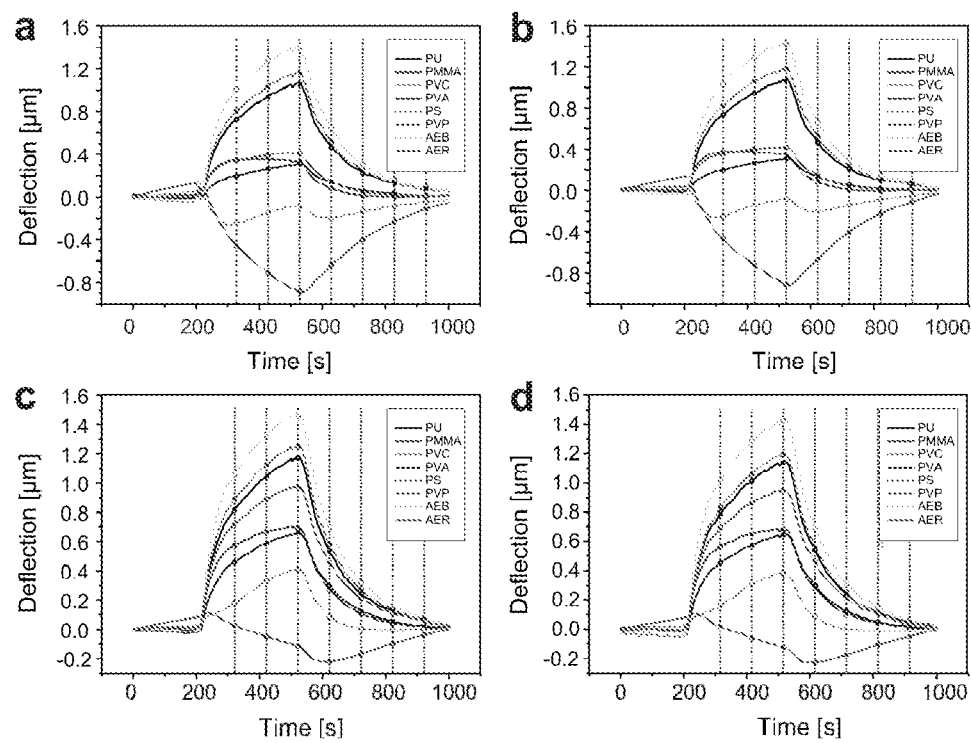
FIGS. 2(a-d) show cantilever deflections for a variety of analyte-reactive coating materials on the cantilever; (a, b) for healthy subjects and (c, d) for exhaled breath gas collected in a bag from subjects suffering from renal disease, according to $3^{rd}$ party reported results.
Figure 3:
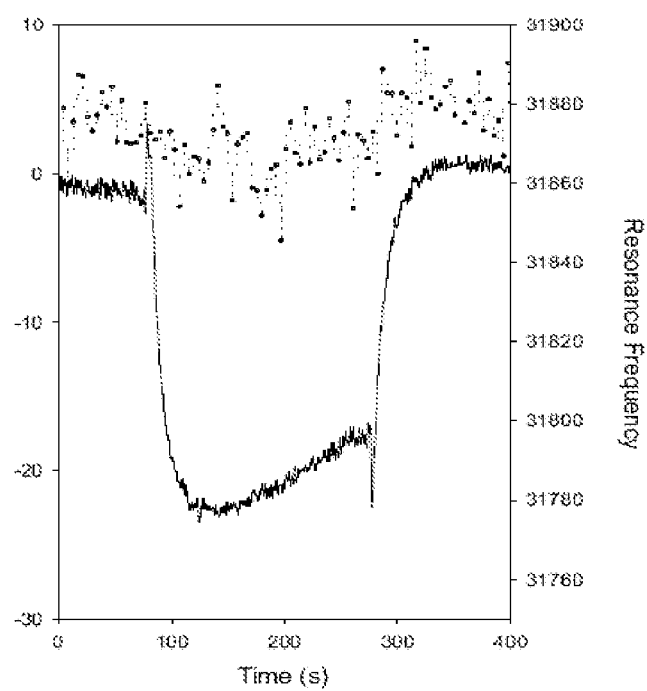
FIG. 3 shows the (negligible) response (dots) of a cantilever to RDX vapor at 290 ppt concentration in ambient air compared to a reference deflection signal, according to $3^{rd}$ party reported results.
Figure 4:
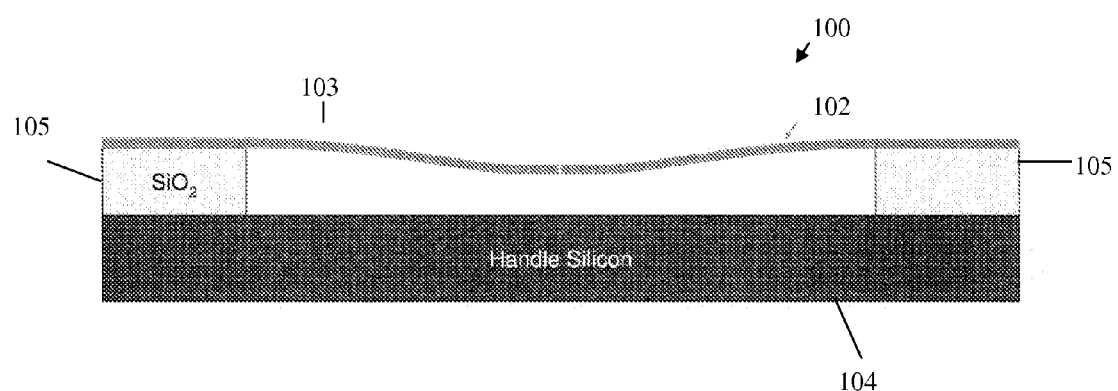
FIG. 4 schematically shows in cross section a composite, analyte sensor including a reactively-coated, double-clamped, statically buckled beam (bridge) resonator that is integrally fabricated on a silicon substrate, according to an exemplary embodiment of the invention.

FIG. 4 schematically shows in cross section a composite, analyte sensor 100 including a reactively-coated (103), double-clamped (105), statically buckled beam (bridge) resonator 102 that is integrally fabricated on a silicon substrate 104. The resonant frequency of these buckled beams has been described by Nayfeh and Emam et al. (A. Nayfeh, W. Kreider and T 1. Anderson, AIAA 1. 33, 1121 (1995); Ali Nayfeh and Samir A. Emam, Nonlinear Dyn. 54, 395 (2008); Samir A. Emam and Ali H. Nayfeh, Composite Structures 88, 636 (2009), the subject matter of which is incorporated herein by reference to the fullest allowable extent).

Figure 5:
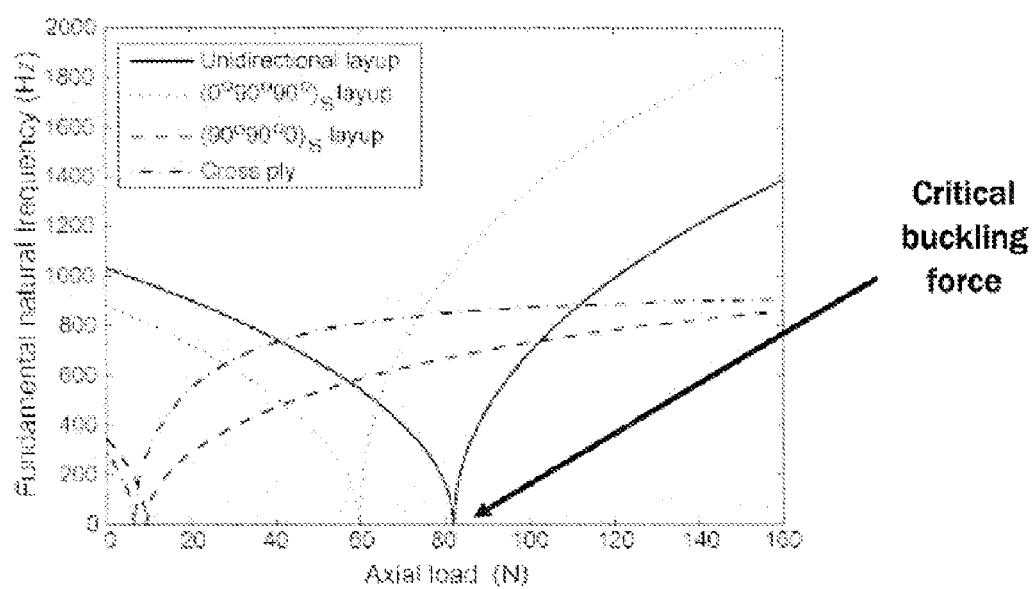
FIG. 5 is a graph of fundamental natural frequency versus axial load illustrating the critical buckling force for a double-clamped beam, according to an illustrative aspect of the invention.

FIG. 5 is a graph of fundamental natural frequency versus axial load (from Nayfeh et al., id) illustrating the critical buckling force for a double clamped beam. As can be seen, there is a rapid change (rise) in resonant frequency with increasing axial load (e.g., due to swelling of the reactive coating in the presence of an analyte) past the critical buckling force. It is this regime of the graph utilized by the embodied invention.

During manufacturing, 100 nm of a porous hygroscopic polymer, tert-butylcalix[6]arene (TBC6A), was deposited on the bridge 102 by thermal evaporation. TBC6A has been considered for detection of TNT vapors but has been shown here to be strongly affected by moisture. Porous polymers commonly swell in proportion to the relative humidity, and the frequency of tensile-stressed doubly-clamped all-polymer beams has been shown to decrease with hygrometric expansion and the associated reduction of the included tension. Swelling of the polymer layer in a composite buckled beam configuration (e.g., FIG. 4; where the buckling occurs as a response to compressive stress), however, produces an axial load that increases the resonance frequency of the fundamental mode.

Figure 6:
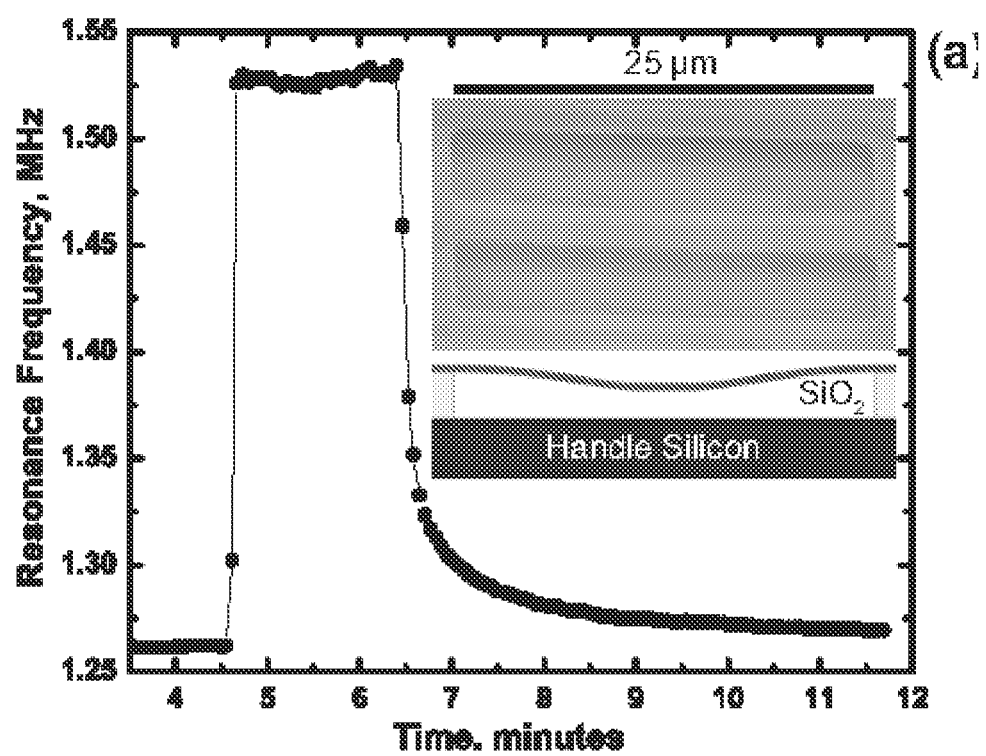
FIG. 6 is a graph showing the fast rise in natural frequency (~1 sec) of a buckled polysilicon microbridge resonator coated in a hygroscopic polymer in response to an increase in relative humidity in nitrogen from dry to around 50%. Inset: SEM and schematic of buckled microbridge, according to an illustrative aspect of the invention.

The frequency response of a coated microbridge to water vapor is shown in FIG. 6. These shifts are counter to the effect of added mass, Δm, which reduces the natural frequency as $$\Delta f = -(f/2)(\Delta m/m_{eff}),$$

where f is the frequency and $m_{eff}$ is the effective mass of the resonator. We estimate that such mass loading decreases the resonance frequency by less than 15 kHz, small compared to the frequency increase observed, and we neglect the added water mass in further calculations assuming the stress-induced frequency rise overwhelms any gravimetric frequency reduction.

According to the embodied invention for a composite beam resonator, the flexural rigidity EI (where E is the Young's modulus; I is the moment of inertia, $I=(1/12) wt^3$; w is the width and t is the thickness) is changed by roughly 2% by the addition of the polymer. Thus in this configuration the main role of the polymer is to alter stress, since the polymer does not significantly affect the flexural rigidity of the composite structure.

Figure 7:
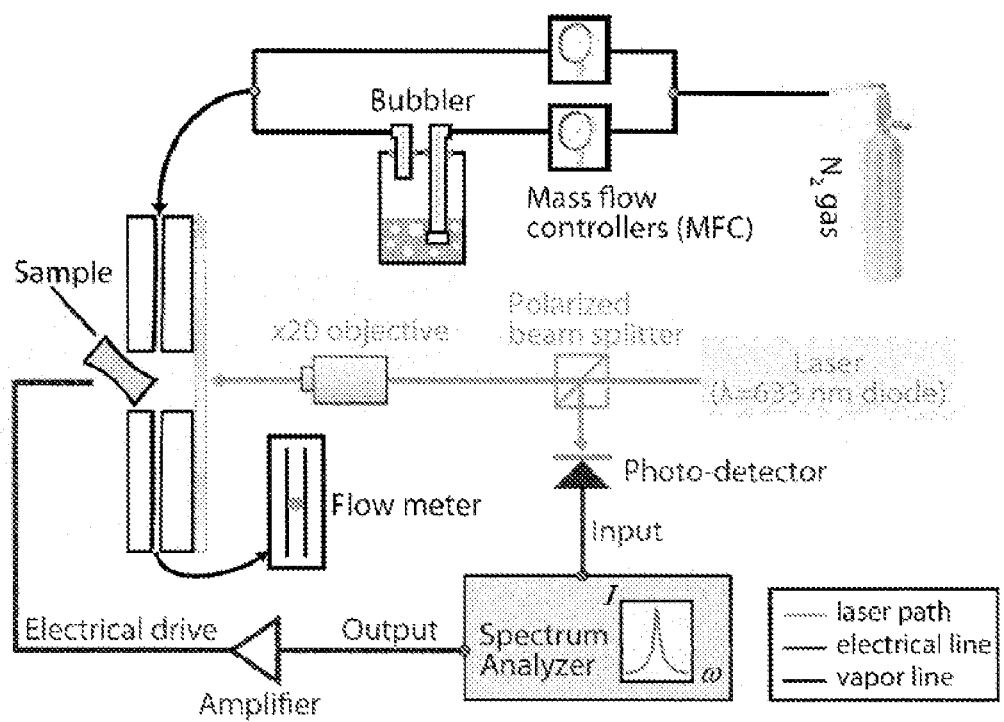
FIG. 7 shows a schematic of an experimental measurement system set-up including electrical drive, optical detection, and vapor delivery systems, according to an illustrative aspect of the invention.

FIG. 7 schematically shows an experimental set-up 700 of a sensor system embodied by the invention. In the experimental set-up, MEMS microbridges were electrostatically driven and their motion detected optically using an interferometric technique through the window of a flow cell. The resonance spectrum of the microbridges was monitored in real-time as the relative humidity of nitrogen was varied between zero and nearly 100%. The relative humidity was controlled using a pair of mass flow controllers that varied the mixing ratios of dry nitrogen and nitrogen aerated through a column of deionized water. Although no humidity standard was used in the experiment, the aerated nitrogen was assumed to be fully saturated.

A resonator was placed in a flow cell of volume 0.7 cm³ under continuous flow conditions of 20 sccm. The characteristic time for the device to stabilize at a new frequency, or its rise time, changes with the flow cell time constant, τ=cell volume/flow rate, for varied gas flow rates, which do not otherwise affect device performance. The rise time was set in this experiment by the time required to replace the gas in the flow cell volume. The characteristic resonator response time was below one second. The longer time constant for the desaturation curve in FIG. 6 is believed to result from the time associated with the systematic drying of the flow lines, although the effect of slower water desorption kinetics could not be ruled out Although beam theory has a long mathematical history, only recently have theorists developed an exact analytical solution to the resonant behavior of buckled beams. If the nonlinear damping and forcing terms are dropped from the differential equation of motion, the resonant frequency relationship to the axial (compressive) load of a buckled beam may be obtained in closed form. For the fundamental mode of the first buckled configuration, $f_0$, in which the embodied devices operate, $$f_0 = [(2/m_l l^2)(S - 4\pi^2 EI/l^2)]^{1/2}, \quad (1)$$

where $m_l$ is the per-length mass, l is the undeformed length of the beam, and S is the axial load on the doubly-clamped beam.

Figure 8:
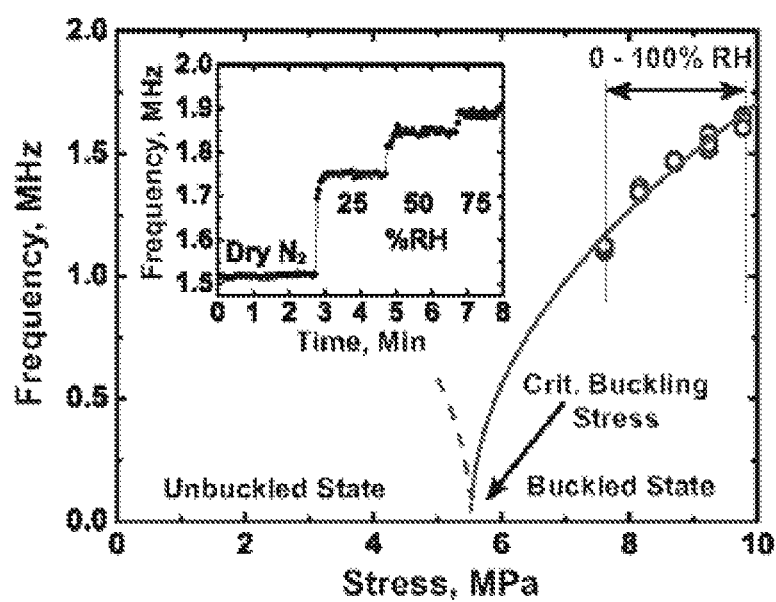
FIG. 8 is a graph showing changes in resonance frequency of a buckled beam. A hygrometric polymer coating expands in proportion to relative humidity (RH). Extrapolation of the fit to the data illustrates potential for high sensitivity near the critical buckling stress. Inset: Resonance frequency shift of a coated microbridge in response to stepped changes in relative humidity; according to an illustrative aspect of the invention.

Ignoring the added water mass and changes in the Young's modulus of the polymer, the stress in the buckled beam may be calculated directly from the resonant frequency measurements, FIG. 8, inset. The second term under the radical in equation (1) describes the critical load at which the beam buckles and where the resonance frequency drops to zero. In the illustrative embodied devices, this load corresponds to an axial (compressive) stress of 5.5 MPa, depicted in the fit of the data in FIG. 8. The inbuilt stress, ~7.6 MPa (that exceeds the buckling stress), results in the static bowing of the beam. Swelling of the polymer when exposed to nitrogen over the full humidity range produced an additional axial stress of around 2.2 MPa. The linearity of the hygrometric expansion of the polymer was generalized to TBC6A from Buchhold (R. Buchhold, A. Nakladal, G. Gerlach, K. Sahre, K. 1. Eichhorn and M. Muller, Microsystem Technologies 5, 3 (1998)) and yields the hygrometric strain $\epsilon_{hyg} = \alpha_{hyg} RH$, where $\alpha_{hyg}$ is the linear coefficient of hygrometric expansion and RH stands for the relative humidity, which varies between zero and one. The stress imparted by polymer swelling is thus $$\sigma_{hyg} = \Delta\sigma = E_{Si}\alpha_{hyg}RH. \quad (2)$$

From equation (2) and the measured change in frequency of a microbridge with RH, we calculated the coefficient of humidity-induced volume expansion to be $\alpha_{hyg}$=180 ppb/% RH. At low RH, the frequency resolution of 3 kHz in our experiment corresponded to a minimum detectable change in stress of ~20 kPa, or 170 ppm of water vapor.

Sensors operated near the critical stress of buckling show increased stress sensitivity since the frequency-stress curve becomes steep as the stress approaches the critical stress (see FIG. 5) and sensitivity goes to infinity at the inflection point of the curve. The maximum stress sensitivity obtainable is likely to be set by geometrical imperfections in the beam, which in effect smooth the transition from the unbuckled to the buckled state. The stress sensitivity of a microbridge varies strongly with the silicon layer thickness, and thus in detector applications these structures benefit from the thin films available in MEMS processing. When optimized, thin microbridges operating near the critical buckling stress could provide a very high sensitivity platform for sensing.

Improved resolution of frequency for operation in gas is possible through improvement of the quality factor, Q, by optimizing the device geometry. Measurements of bare and coated microbridges in vacuum yielded nominal Q of 4000 and 400, respectively, compared to a quality factor of at most 10 in air (Q=3 for 6 μm wide beams; Q=10 for 2 μm wide beams). This suggests that acoustic dissipation (viscous damping) rather than intrinsic materials loss is the primary energy dissipation mechanism at atmospheric pressure. The quality factor of 400 for the composite structure implicates intrinsic losses in the polymer as the predominant dissipation mechanism in vacuum.

Microbridges enable direct transduction of stress variation into the frequency or phase domain, which is advantageous for its high measurement accuracy and for integration of sensors into radio frequency circuitry. Structures created from doped silicon are compatible with the electrical detection techniques introduced by Truitt et. al. (Patrick, A. Truitt, Jared B. Hertzberg, C. C. Huang, Kamil J. Ekinci and Keith C. Schwab, Nano Letters 7, 120 (2007)), as well as amenable to readout via embedded piezoelectric elements. Because of their different responses to stress, operation of microbridges in conjunction with cantilevers or other variously coated, sensitive structures could contribute an orthogonal response to assist in unique identification of analytes in electronic nose applications.

Resonant microbridges coated with TBC6A can be sensitive to relative humidity. While this material has been shown to be sensitive to other volatile compounds, the use of hygroscopic materials for detection may require control for moisture. Common mode canceling can be employed to account for environmental factors such as atmospheric pressure or temperature variations.

Doped polysilicon resonators such as embodied herein are compatible with electrical detection and integration into industrial CMOS processes (see J. D. Cross, B. R. Ilic, M. K. Zalalutdinov, W. Zhou, J. W. Baldwin, B. H. Houston, H. G. Craighead and J. M. Parpia, Appl. Phys. Lett. 95, 133 113 (2009); M Villarroya, E. Figueras, J. Montserrat, J. Verd, J. Teva, G. Abadal, F P. Murano, J. Esteve and N. Barniol, J Micromech Microengineering 16, 2203 (2006); J. Voiculescu, M Zaghloul, R. A. McGill, E. J. Houser and G. K. Fedder, IEEE Sensors Journal 5, 641 (2005)), where stressed polysilicon layers are common. Fabricated through simple top-down processing, microbridge sensors represent an excellent example of advantageous scaling in MEMS. Resonant detection of vapor through the mechanism of stress has the potential to improve real-time atmospheric gas sensing technology.

Exemplary Resonator Design

Figure 9:
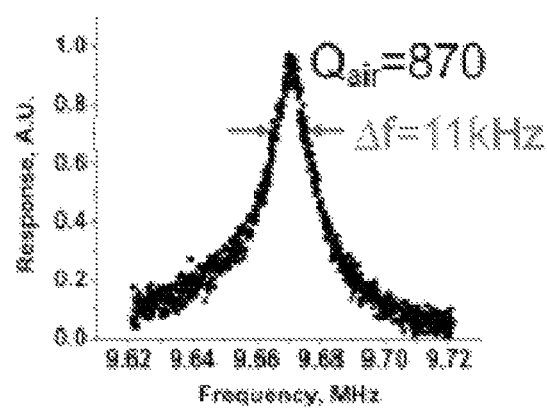
FIG. 9 is a graph showing an approximately 10 MHz resonance obtained in air; Q=870; frequency shifts can be resolved to ~10 Hz, according to an illustrative aspect of the invention.
Figure 10:
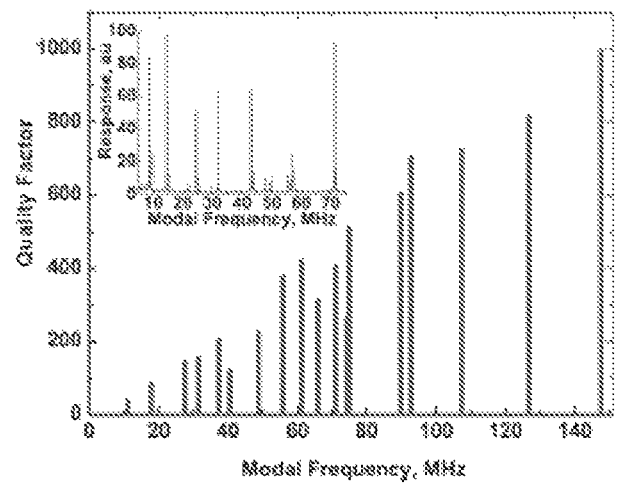
FIG. 10 is a chart showing that device Q is enhanced when resonators are operated at higher harmonics, according to an illustrative aspect of the invention.

FIGS. 6 and 8 show signals showing the resonant frequency increase of a Buckled, doubly-clamped beam when exposed to water vapor. The device Q is approximately 4 when operated in ambient air. By operating close to the buckling transition, a large frequency shift can be induced through a relatively small change in stress (e.g., 3 MPa produced a 40% change in frequency). In FIG. 9 we demonstrate a prototype non-buckled resonator operating with a Q of 870 in air. Such a device would have 20× better sensitivity than that shown in FIG. 6. Further improvements may be realized by optimizing design, decreasing the phenomenon termed "squeeze film damping" where energy is transferred to the gas trapped under the moving device, thus widening the response curve. Device Q is also enhanced when resonators are operated at higher harmonics as illustrated in FIG. 10. This will boost the Q to ~2000 and allow for analyte resolution below the 100 ppm level, necessary to resolve meaningful changes in nitrous oxide from breath gas.

Integration

Figure 11:
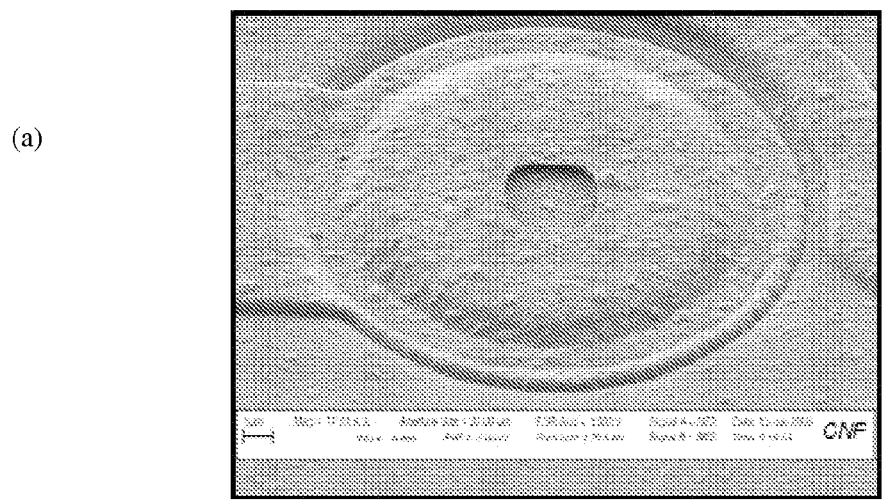
FIGS. 11 (a, b, c), respectively, show a) an upward buckled "drum" resonator fabricated in a standard commercial foundry; b) the device is embedded in a drive detector/circuit; c) a buckled bridge resonator (from the same process) with characteristics similar to that shown in FIG. 4, according to an exemplary aspects of the invention.
Figure 11:
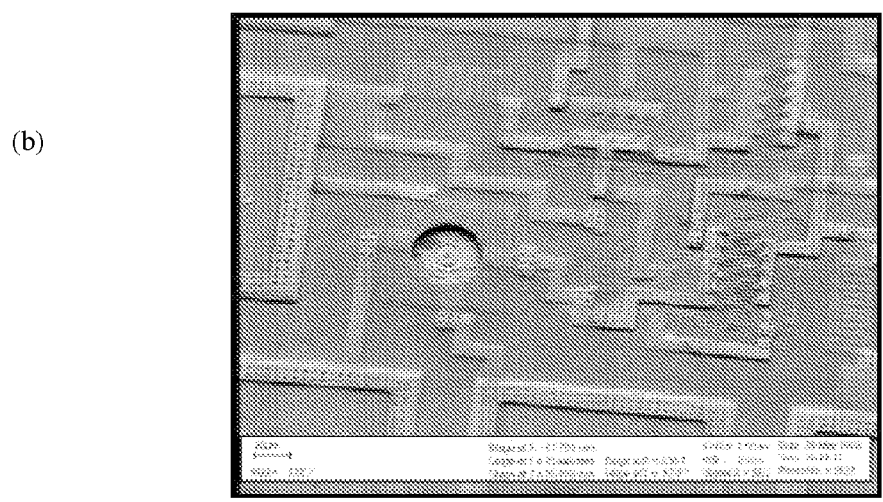
Figure 11:
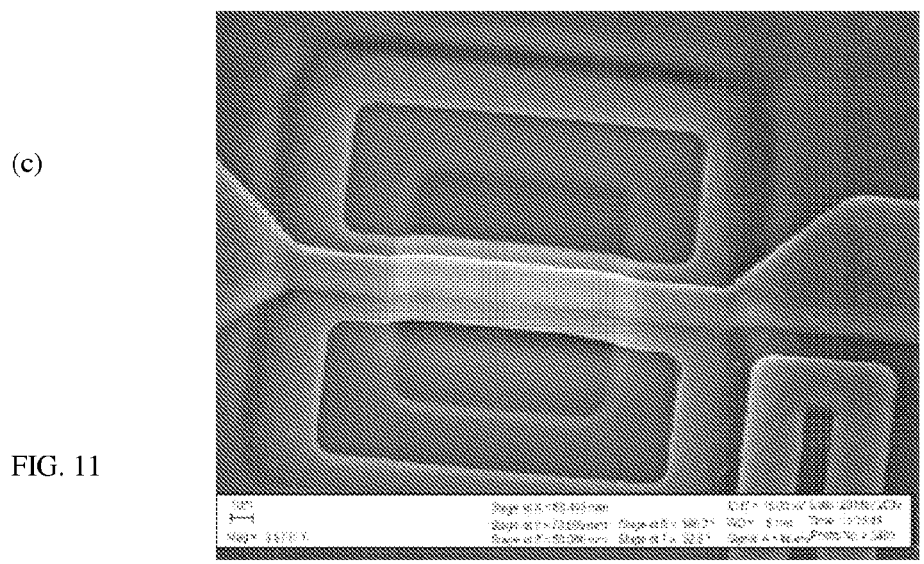

To realize the size and power advantages of micromechanical resonators over macroscopic devices, devices should be readily fabricated without access to custom processes, so that they can be incorporated into circuits ubiquitously. FIGS. 11(a, b, c) illustrate resonators that have high Q even when operated in air, which are fabricated under compressive stress (thus being readily adaptable to stress based sensing), and are buckled. These and similar designs can be implemented using the ON Semiconductor process at the MOSIS foundry. Another feature of the structures shown in FIG. 11 realized in the commercial foundry is that by design they are immune to stiction. (When a device is immersed in liquid (e.g., when it is being functionalized), as the liquid evaporates, surface tension forces lead to collapse of the structures or adhesion to the lower layer (stiction), preventing the device from resonating). Stiction can also be avoided by a critical point drying process that adds an extra processing step and cost to the fabrication.

Functionalization

Reported earlier work utilized a variety of polymer coating functionalizations that demonstrate stress modification upon exposure to various breath gas analytes. In an aspect of the embodied invention, individual coatings can be deposited on different resonators, the chips diced, and an array of differently functionalized resonators assembled. Each such array may include a non-functionalized resonator as a control device for background differentiation (e.g., for temperature, pressure or NO/ethane content in inhaled air). It may be possible to develop a mask for coating, though other techniques (such as ink jet type printing) may be applicable. We have already demonstrated the use of pipetting and spinning techniques to successfully coat buckled beam resonators.

To take advantage of the rapid response rate of the M/NEMS resonators, closed loop operation of resonators using PLLs can be implemented to allow continuous monitoring of the resonators' frequency.

All references, including publications, patent applications and patents cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening.

The recitation of ranges of values herein are merely intended to serve as a shorthand method of referring individually to each separate value falling within the range, unless otherwise indicated herein, and each separate value is incorporated into the specification as if it were individually recited herein.

All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not impose a limitation on the scope of the invention unless otherwise claimed.

No language in the specification should be construed as indicating any non-claimed element as essential to the practice of the invention.

It will be apparent to those skilled in the art that various modifications and variations can be made to the present invention without departing from the spirit and scope of the invention. There is no intention to limit the invention to the specific form or forms disclosed, but on the contrary, the intention is to cover all modifications, alternative constructions, and equivalents falling within the spirit and scope of the invention, as defined in the appended claims. Thus, it is intended that the present invention cover the modifications and variations of this invention provided they come within the scope of the appended claims and their equivalents.

We claim:

1. An analyte sensor, comprising:
a substrate;
a composite micro- or nano-electro-mechanical (MEMS; NEMS) resonator comprising a structure configured to be driven into resonance and which is double-clamped such that it is coupled to the substrate at a plurality of edge locations of the structure, and a volume-sensitive reactive coating covering at least a portion of a surface of the structure, which is characterized by a volumetric change upon exposure to a given analyte, wherein the volumetric change comprises a change in a stress value of the resonator, further wherein the change in the stress value of the resonator comprises a measurable change in a resonance frequency of the resonator, further wherein the resonator is in a compressively-stressed, statically-buckled state that is not at a buckling transition point of the resonator when driven into resonance, wherein the resonator is in the form of a dome or drum.

2. The sensor of claim 1, further comprising a plurality of the composite MEMS or NEMS resonators, each of which is characterized by a different resonant frequency.

3. The sensor of claim 1, wherein the volume-sensitive reactive coating is a hygroscopic polymer.

4. A method for sensing an analyte, comprising:
providing a composite micro- or nano-electro-mechanical (MEMS; NEMS) resonator comprising a structure configured to be driven into resonance and which is double-clamped such that it is coupled to the substrate at least two edge locations of the structure, and a volume-sensitive reactive coating covering at least a portion of a surface of the structure, which is characterized by a volumetric change upon exposure to a given analyte, said volumetric change giving rise to a change in a stress value of the resonator providing a measurable change in a resonance frequency of the resonator, further wherein the resonator is in a compressively-stressed, statically-buckled state that is not at a buckling transition point of the resonator;
driving the resonator to resonate at a resonance frequency;
exposing the resonator to a given gas sample wherein the volume-sensitive reactive coating undergoes an increase or decrease in volume; and
measuring the change in the resonance frequency of the resonator at a selected time after exposing the resonator to the given gas sample.

5. The method of claim 4, further comprising determining an amount of the analyte in the gas sample.

6. The method of claim 4, further comprising sensing the presence of the analyte in the gas sample in a time period less than one second.

7. The method of claim 4, further comprising providing a plurality of the composite MEMS or NEMS resonators, each of which is resonating at a different resonant frequency.

8. The method of claim 4, further comprising exposing the resonator to a breath sample of a living subject.

9. The method of claim 5, further comprising determining less than 100 parts per million (ppm) of the analyte.

10. The method of claim 4, further comprising measuring one of an increase and a decrease of the resonance frequency of the resonator at the selected time after exposing the resonator to the given gas sample.

* * * * *